(12) United States Patent
Ao et al.

(10) Patent No.: US 9,434,999 B1
(45) Date of Patent: Sep. 6, 2016

(54) SPECIFIC DETECTION OF ORGANISMS DERIVED FROM A SAMPLE

(71) Applicant: Great Basin Scientific, Inc., West Valley City, UT (US)

(72) Inventors: Wanyuan Ao, Salt Lake City, UT (US); Robert D. Jenison, Boulder, CO (US); Jamie Purcell, South Jordan, UT (US)

(73) Assignee: Great Basin Scientific, Inc., Salt Lake City, UT (US)

( * ) Notice: Subject to any disclaimer, the term of this patent is extended or adjusted under 35 U.S.C. 154(b) by 0 days.

(21) Appl. No.: 14/883,918

(22) Filed: Oct. 15, 2015

Related U.S. Application Data

(62) Division of application No. 14/752,345, filed on Jun. 26, 2015.

(51) Int. Cl.
*C12Q 1/68* (2006.01)
*C12P 19/34* (2006.01)

(52) U.S. Cl.
CPC .................................. *C12Q 1/689* (2013.01)

(58) Field of Classification Search
None
See application file for complete search history.

(56) References Cited

U.S. PATENT DOCUMENTS

| | | | |
|---|---|---|---|
| 5,565,340 A | 10/1996 | Chenchik et al. | |
| 5,652,096 A | 7/1997 | Cimino | |
| 8,071,338 B2 | 12/2011 | Newton | |
| 8,268,579 B2 | 9/2012 | Edberg | |
| 2010/0221717 A1 | 9/2010 | Chen et al. | |
| 2012/0214160 A1 | 8/2012 | Deng et al. | |
| 2013/0177946 A1 | 7/2013 | Chen et al. | |

FOREIGN PATENT DOCUMENTS

| | | |
|---|---|---|
| WO | WO 2012/162621 A1 | 11/2012 |
| WO | WO 2013/026027 A1 | 2/2013 |
| WO | WO 2013/079212 A1 | 6/2013 |

OTHER PUBLICATIONS

Celt, et al., "A rapid and versatile method to synthesize internal standards for competitive PCR," *Nucleic Acids Research*, 21(4):1047 (1993).
Guenthner, et al., "Quantitative, Competitive PCR Assay for HIV-1 Using a Microplate-Based Detection System," *BioTechniques*, 24:810-816 (1998).
Park, et al., "Comparison of phenotypic and genotypic methods for the species identification of coagulase-negative staphylococcal isolates from bovine intrammary infections," *Veterinary Microbiology*, 147:142-148 (2011).
York, et al., "Comparison of mecA with Standard Susceptibility Testing Methods to Determine Methicillin Resistance in Coagulase-Negative Staphylococci," *Journal of Clinical Microbiology*, 34(2):249-253 (1996).

*Primary Examiner* — Young J Kim
(74) *Attorney, Agent, or Firm* — Ryan L. Marshall; Robert D. Shereda; Brinks Gilson & Lione

(57) ABSTRACT

Methods, materials, and kits for distinguishing a population of cells or organisms truly present in a clinical specimen from contaminating cells or organisms is disclosed. The methods and kits use a suppressor to avoid false positive detection of contaminants in nucleic acid amplification reactions.

21 Claims, 2 Drawing Sheets

SEQUENCE LISTING

<160> NUMBER OF SEQ ID NOS: 22

<210> SEQ ID NO 1
<211> LENGTH: 74
<212> TYPE: DNA
<213> ORGANISM: Artificial Sequence
<220> FEATURE:
<223> OTHER INFORMATION: TufSyn2: nucleotide sequence

<400> SEQUENCE: 1
tgaacgtggt cgaatcaaag ctagtgaaga agttgacgta aaacaactgt tccatgtgct        60
gaaatgttcc gtaa                                                         74

<210> SEQ ID NO 2
<211> LENGTH: 70
<212> TYPE: DNA
<213> ORGANISM: Artificial Sequence
<220> FEATURE:
<223> OTHER INFORMATION: MecSyn3: nucleotide sequence

<400> SEQUENCE: 2

```
tcaggaacgg caatccaccc tcaaacaggt gatgacgtct atccattaat gtgtggcctg    60
agtaacgaag                                                            70

<210> SEQ ID NO 3
<211> LENGTH: 70
<212> TYPE: DNA
<213> ORGANISM: Artificial Sequence
<220> FEATURE:
<223> OTHER INFORMATION: NucSyn1: nucleotide sequence

<400> SEQUENCE: 3
tcaggaacgg caatccaccc tcaaacaggt gatgacgtct atccattaat gtgtggcctg    60
agtaacgaag                                                            70

<210> SEQ ID NO 4
<211> LENGTH: 70
<212> TYPE: DNA
<213> ORGANISM: Artificial Sequence
<220> FEATURE:
<223> OTHER INFORMATION: TufSyn10: nucleotide sequence

<400> SEQUENCE: 4
tcaggaacgg caatccaccc tcaaacaggt gatgacgtct atccattaat gtgtggcctg    60
agtaacgaag                                                            70

<210> SEQ ID NO 5
<211> LENGTH: 120
<212> TYPE: DNA
<213> ORGANISM: Artificial Sequence
<220> FEATURE:
<223> OTHER INFORMATION: NucSyn3: nucleotide sequence

<400> SEQUENCE: 5
gacaaaggtc aaagaactga taaatatgga cgtggcttag cgacctgaca gtacaatatc    60
aagacgacta tgacaagacg aggtacgaag ctttagttcg tcaaggcttg gctaaagttg   120

<210> SEQ ID NO 6
<211> LENGTH: 30
<212> TYPE: DNA
<213> ORGANISM: Artificial Sequence
<220> FEATURE:
<223> OTHER INFORMATION: mecAf1145: nucleotide sequence

<400> SEQUENCE: 6
tcaggtactg ctatccaccc tcaaacaggt                                      30

<210> SEQ ID NO 7
<211> LENGTH: 37
<212> TYPE: DNA
<213> ORGANISM: Artificial Sequence
<220> FEATURE:
<223> OTHER INFORMATION: mecAr1244; nucleotide sequence

<400> SEQUENCE: 7
cttcgttact catgccatac ataaatggat agacgtc                              37

<210> SEQ ID NO 8
<211> LENGTH: 37
<212> TYPE: DNA
<213> ORGANISM: Artificial Sequence
<220> FEATURE:
<223> OTHER INFORMATION: tuf430L: nucleotide sequence

<400> SEQUENCE: 8
```
cttcgttact catgccatac ataaatggat agacgtc                                37

<210> SEQ ID NO 9
<211> LENGTH: 34
<212> TYPE: DNA
<213> ORGANISM: Artificial Sequence
<220> FEATURE:
<223> OTHER INFORMATION: tuf426f11: nucleotide sequence

<400> SEQUENCE: 9
gtgttgaacg tggtcaaatc aaagttggtg aaga                                   34

<210> SEQ ID NO 10
<211> LENGTH: 33
<212> TYPE: DNA
<213> ORGANISM: Artificial Sequence
<220> FEATURE:
<223> OTHER INFORMATION: tuf527v1: nucleotide sequence

<400> SEQUENCE: 10
atttacggaa catttcaaca cctgtaacag ttg                                    33

<210> SEQ ID NO 11
<211> LENGTH: 40
<212> TYPE: DNA
<213> ORGANISM: Artificial Sequence
<220> FEATURE:
<223> OTHER INFORMATION: mec-3F: nucleotide sequence

<400> SEQUENCE: 11
caaaatgaaa caaggagaaa ctggcagaca aattgggtgg                             40

<210> SEQ ID NO 12
<211> LENGTH: 40
<212> TYPE: DNA
<213> ORGANISM: Artificial Sequence
<220> FEATURE:
<223> OTHER INFORMATION: mec-3RB: nucleotide sequence

<400> SEQUENCE: 12
acactttacc tgagattttg gcattgtagc tagccattcc                             40

<210> SEQ ID NO 13
<211> LENGTH: 42
<212> TYPE: DNA
<213> ORGANISM: Artificial Sequence
<220> FEATURE:
<223> OTHER INFORMATION: nuc-6F: nucleotide sequence

<400> SEQUENCE: 13
gacaaaggtc aaagaactga taaatatgga cgtggcttag cg                          42

<210> SEQ ID NO 14
<211> LENGTH: 36
<212> TYPE: DNA
<213> ORGANISM: Artificial Sequence
<220> FEATURE:
<223> OTHER INFORMATION: nuc-6RB: nucleotide sequence

<400> SEQUENCE: 14
caactttagc caagccttga cgaactaaag cttcgt                                 36

<210> SEQ ID NO 15
<211> LENGTH: 34
<212> TYPE: DNA

```
<213> ORGANISM: Artificial Sequence
<220> FEATURE:
<223> OTHER INFORMATION: tuf-3F: nucleotide sequence

<400> SEQUENCE: 15
ctacaggccg tgttgaacgt ggtcaaatca aagt                              34

<210> SEQ ID NO 16
<211> LENGTH: 49
<212> TYPE: DNA
<213> ORGANISM: Artificial Sequence
<220> FEATURE:
<223> OTHER INFORMATION: tuf-3RB: nucleotide sequence

<400> SEQUENCE: 16
cagcttcagc gtagtctaat aatttacgga acatttcaac acctgtaac              49

<210> SEQ ID NO 17
<211> LENGTH: 33
<212> TYPE: DNA
<213> ORGANISM: Artificial Sequence
<220> FEATURE:
<223> OTHER INFORMATION: nuc-1FB: nucleotide sequence

<400> SEQUENCE: 17
gctcagcaaa tgcatcacaa acagataacg gcg                               33

<210> SEQ ID NO 18
<211> LENGTH: 47
<212> TYPE: DNA
<213> ORGANISM: Artificial Sequence
<220> FEATURE:
<223> OTHER INFORMATION: nuc-1R: nucleotide sequence

<400> SEQUENCE: 18
ctaagccacg tccatattta tcagttcttt gacctttgtc aaactcg                47

<210> SEQ ID NO 19
<211> LENGTH: 46
<212> TYPE: DNA
<213> ORGANISM: Artificial Sequence
<220> FEATURE:
<223> OTHER INFORMATION: femB-F6: nucleotide sequence

<400> SEQUENCE: 19
acagcaacat caatgtttat atgttaaatt agatccgtat tggtta                 46

<210> SEQ ID NO 20
<211> LENGTH: 33
<212> TYPE: DNA
<213> ORGANISM: Artificial Sequence
<220> FEATURE:
<223> OTHER INFORMATION: femB-R4: nucleotide sequence

<400> SEQUENCE: 20
ggcatcattt ttctcgcgac cttcaaatgg cac                               33

<210> SEQ ID NO 21
<211> LENGTH: 24
<212> TYPE: DNA
<213> ORGANISM: Artificial Sequence
<220> FEATURE:
<223> OTHER INFORMATION: femB-CP2: nucleotide sequence

<400> SEQUENCE: 21
ggcacgatat ctttatyata taga                                         24
```

<210> SEQ ID NO 22
<211> LENGTH: 105
<212> TYPE: DNA
<213> ORGANISM: Artificial Sequence
<220> FEATURE:
<223> OTHER INFORMATION: FemBSyn1: nucleotide sequence

<400> SEQUENCE: 22
tttacagcaa catcaatgtt tatatgttaa attagatccg tattggttat ctcagctaca      60
agacgatcag tgccatttga aggtcgcgag aaaaatgatg cccta                    105

SPECIFIC DETECTION OF ORGANISMS DERIVED FROM A SAMPLE

REFERENCE TO EARLIER FILED APPLICATION

This application is a division of and claims the benefit of the filing date of U.S. patent application Ser. No. 14/752,345, filed Jun. 26, 2015, the disclosure of which is incorporated, in its entirety, by this reference.

FIELD OF INVENTION

This application describes methods, materials, and kits for determining whether a target population is truly present in non-contaminating quantities in a clinical specimen. The methods, materials, and kits may be used for distinguishing viable or actively growing populations of cells or organisms from non-viable or non-cultured organisms in a clinical sample that optionally has undergone a subsequent step of growth in a culture medium.

BACKGROUND

Detection of bacterial species present in clinical samples can direct therapeutic decision making, so tests with high sensitivity and specificity are required. Bacteria such as *staphylococci* that may cause disease, however, are also ubiquitously present in the environment and, if inadvertently introduced into a sample or test reagent, result in false positive detection. Numerous approaches have addressed the question of determining if a given target population present in a clinical specimen is potentially disease causing using quantitative, real-time polymerase chain reaction (qPCR). In one qPCR approach, a cycle threshold (Ct) is established whereupon any nasal swab sample that generates detectable signal from amplification of *Staphylococcus aureus* target nucleic acid present in the sample at a cycle number greater than Ct is deemed non-viable, a contaminant, or at a level too low to cause disease. Another method exposes samples containing cells or viruses to propidium monoazide, which can crosslink DNA in lysed cells or RNA in inactive viruses when illuminated with light, but not in intact or viable cells or viruses. The resulting cross-linked DNA or RNA cannot be amplified. Therefore, in this method, any detected amplified DNA or RNA can only be derived from intact cells or viruses.

Each of these methods, however, comes with its own drawbacks. For example, in the cycle threshold method, various components in a clinical sample may impact the efficiency of the qPCR reaction, creating imprecision in the Ct value likely resulting in lower detection sensitivity. In the case of the crosslinking method, only cells with compromised membranes or cell walls will have their DNA exposed for crosslinking treatment, thereby increasing the signal generated during cycling by non-dividing or dead but unlysed or intact cells. Additionally, these methods are not useful in approaches that are non-quantitative and do not detect amplification in real-time. In these approaches, generally referred to as end point detection, nucleic acids are amplified, and the resulting product is detected after completion of the amplification reaction. End point detection detects whether or not a target nucleic acid has been amplified to detectable levels. Differences in sample matrix from sample to sample such as concentration of components that can inhibit amplification reactions in blood or stool can affect the speed of amplifying nucleic acids to detectable levels. Because of this, one cannot easily determine when to stop the amplification reaction such that differences in starting amounts of nucleic acid targets are reflected in the amount of target nucleic acid amplified. Additionally, end point detection methods such as planar surface DNA arrays are generally only semi-quantitative with poor dynamic range of quantitation. As a result, differences in amount of nucleic acid target present in a sample cannot be reliably used to distinguish viable and non-viable organisms using end point detection.

Therefore, there is a need for an improved method of distinguishing between viable, truly infecting pathogens and dead or contaminating pathogens, especially in end point detection approaches.

BRIEF SUMMARY

In one aspect, a kit for determining whether a sample contains a threshold amount of a target cell population is disclosed. The kit includes a signal suppressor comprising a suppressor nucleic acid; an upstream DNA primer for annealing to the suppressor nucleic acid at an upstream annealing site; a downstream DNA primer for annealing to the suppressor nucleic acid at a downstream annealing site; wherein the upstream DNA primer can anneal to a target cell nucleic acid at an upstream annealing site, and the downstream DNA primer can anneal to the target cell nucleic acid at a downstream annealing site, the upstream and downstream DNA primers each having sequences that, upon subjecting the sample to a nucleic acid amplification process, cause the upstream and downstream DNA primers to amplify a sequence between the upstream and downstream annealing sites of the nucleic acids in both the signal suppressor and the target cell population, and wherein the signal suppressor is provided in a sufficient quantity to eliminate detectable levels of amplification of target cell nucleic acid if the target cell population is present below a threshold amount.

In some embodiments, the signal suppressor is a double-stranded DNA. In some embodiments, the signal suppressor is a single-stranded DNA.

In some embodiments, the kit also includes DNA polymerase.

In some embodiments, the nucleic acid amplification process is helicase dependent amplification. In some embodiments, the kits includes a deoxyribonucleotide triphosphate mixture. In some embodiments, the DNA primers are biotin-labeled. In some embodiments, the signal suppressor comprises a synthetic DNA template. In some embodiments, the DNA of the target cell population is genomic DNA of a *Staphylococcus* species. In some embodiments, the signal suppressor is selected from *Staphylococcus succinus* and *Staphylococcus muscae*. In some embodiments, the kid includes an array of immobilized DNA capture probes for hybridizing to the DNA of the target cell population.

In some embodiments, the sample comprises cultured blood. In some embodiments, the upstream and downstream DNA primers amplify a mecA-specific gene sequence. In some embodiments, the upstream and downstream DNA primers amplify a tuf-specific gene sequence. In some embodiments, the upstream and downstream DNA primers amplify a nuc-specific gene sequence.

In another aspect, a method of determining whether a sample contains a threshold amount of a target cell population is disclosed. The method includes identifying at least one type of target cell to detect from a sample; identifying a limit of detection above which amplification of a nucleic acid from the target cell is noncontaminating; adding at least one signal suppressor nucleic acid for each potential cell type to the sample in a quantity sufficient to ensure that amplification of each potential cell type will not proceed to detectable levels if the cell type is present in a quantity below the limit of detection; amplifying the nucleic acid of the target cell with a DNA polymerase, a deoxyribonucleotide triphosphate mixture, and at least one pair of DNA primers, each of the pair of DNA primers having a sequence that anneals to a signal suppressor nucleic acid and the target cell nucleic acid; and detecting a signal from the product of the nucleic acid amplification to determine whether the cell type is present.

In some embodiments, amplifying the nucleic acid uses helicase dependent amplification. In some embodiments, amplifying the nucleic acid uses polymerase chain reaction.

In some embodiments, the detection step further comprises detecting precipitate from a reaction product catalyzed by horseradish peroxidase activity.

In some embodiments, the cell type comprises a *Staphylococcal* species present in a positive blood culture, and the limit of detection is about 10,000 to about 100,000 colony forming units per milliliter. In some embodiments, the cell type is a *Staphylococcal* species present in a blood culture, and the limit of detection is about 500 colony forming units. In some embodiments, the sample includes human blood.

In some embodiments, the DNA primers amplify the target cell nucleic acid at an amplification rate equal to a rate of signal suppressor amplification, and the quantity of signal suppressor required to achieve a desired threshold amount is the product of a number of a primer molecules and a threshold amount divided by a lower limit of detection.

In some embodiments, the DNA primers amplify the target cell nucleic acid at a PCR efficiency equal to a PCR efficiency of the signal suppressor, and the quantity of signal suppressor required to achieve a required threshold is the product of a number of a primer molecules and a threshold amount divided by a lower limit of detection.

In some embodiments, the amplification is polymerase chain reaction and the DNA primers amplify the target cell nucleic acid at a PCR efficiency different from the PCR efficiency of the signal suppressor, and the quantity of signal suppressor required to achieve a desired threshold is the product of a number of a primer molecules and a threshold amount multiplied by a quantity of an efficiency of amplification of the target population raised to the nth power, n being the number of cycles of the polymerase chain reaction, and divided by the lower limit of detection multiplied by an efficiency of the amplification of the signal suppressor raised to the nth power.

In some embodiments, the amplification is helicase dependent amplification, and the DNA primers amplify the target cell nucleic acid at amplification rate different from the amplification rate of the signal suppressor, and the quantity of signal suppressor required to achieve a desired threshold is the product of a number of a primer molecules and a threshold amount multiplied by the exponential of the difference between the amplification rate of the target cell multiplied by amplification time and the amplification rate of the suppressor multiplied by amplification time and divided by the lower limit of detection.

In some embodiments, the method further includes identifying a threshold amount of the target cell population above which the population is considered non-contaminating. In some embodiments, the method further includes determining the lower limit of detection of a detection method utilized to analyze the product of the nucleic acid amplification.

In some embodiments, the method includes determining an amplification rate of the target cell nucleic acid. In some embodiments, the method includes determining an amplification rate of the signal suppressor.

In another aspect, a method of determining whether a sample contains at least 500 colony forming units per milliliter of *Staphylococcus* is disclosed. The method includes providing a sample suspected of having *Staphylococcus*; adding at least one signal suppressor nucleic acid to the sample in a quantity sufficient to ensure that amplification of a nucleic acid sequence from *Staphylococcus* will not proceed to detectable levels unless there are at least 500 colony forming units present; subjecting the sample to a nucleic acid amplification using an amplification mixture comprising a DNA polymerase, a deoxyribonucleotide triphosphate mixture, and at least one pair of DNA primers, each of the pair of DNA primers having a sequence that anneals to the signal suppressor nucleic acid and the nucleic acid sequence from *Staphylococcus*; and detecting a signal from the product of the nucleic acid amplification to determine whether at least 500 colony forming units of *Staphylococcus* are present.

In some embodiments, the nucleic acid amplification is a helicase-dependent amplification. In some embodiments, the nucleic acid amplification is a polymerase chain reaction.

In some embodiments, the DNA primers are biotinylated.

In some embodiments, the step of detecting a signal comprises hybridization of the product of the nucleic acid amplification protocol to immobilized complementary DNA strands to yield a hybridized sample.

In some embodiments, wherein the DNA primers amplify a mecA-specific gene sequence. In some embodiments, the DNA primers amplify a tuf-specific gene sequence. In some embodiments, the DNA primers amplify a nuc-specific gene sequence.

DEFINITIONS

Figure 1:
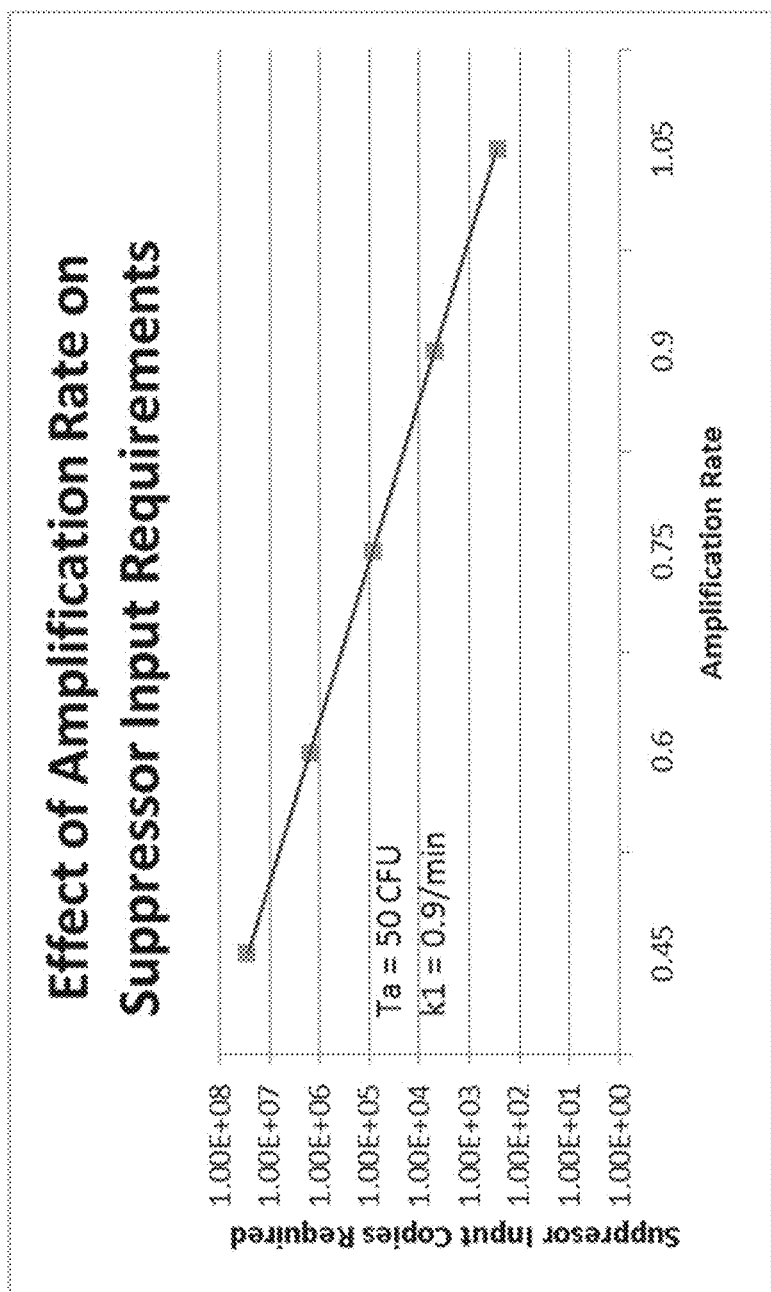
FIG. 1 is a graphical representation which provides an example of the amount of signal suppressor required to eliminate detection as a function of amplification rate according to one aspect of the invention.

As used herein, the term "target population" means a population of organisms, cells, viruses, or any combination of these which is thought to be or known to be present in a sample. The target population can be a cell line; a single cell type; one or more strains of virus; one or more genus, species, subspecies, or strains of bacterium; one or more genus, species, or subspecies of single-celled eukaryote; one or more genus, species, or subspecies of multicellular eukaryote; genomic DNA or cellular RNA including messenger RNA (mRNA), ribosomal RNA (rRNA), and transfer RNA (tRNA) or combinations of any of the foregoing.

As used herein, the term "signal suppressor" means an organism or synthetic nucleic acid template that has significant homology or complementarity to primer or probe sequences designed to amplify sequence(s) from a target population of interest. The regions of primer homology are optionally, but preferably, at the 5' and 3' ends of the signal suppressor. Intervening sequence exists between these homologous primer binding regions that can be amplified by the action of DNA replicating enzymes in an amplification mixture. The amplified region within the signal suppressor can have distinct sequence from one present in the target population to permit identification of the target population without risk of a false positive test results from the signal suppressor. The signal suppressor may optionally be an intact organism or cell, a lysed cell, genomic DNA, or a synthetic nucleic acid template (further defined below). The signal suppressor may also be an RNA template or rRNA, mRNA, or tRNA. The RNA suppressor would be useful for assays utilizing either RNA or DNA replicating enzymes in an amplification mixture. In assays designed to directly detect a target within a sample when no target amplification occurs, the signal suppressor would have significant homology or complementarity to probe(s) used for detection within the assay as a means to suppress signal. However, in these direct detection assays the signal suppressor would not contain sequence amplified by the action of nucleic acid replicating enzymes.

As used herein, the term "significant homology" means the degree of complementarity to the DNA primers used to amplify target sequence is sufficient to create a "threshold amount" (defined below) required for detection of a target population. In some embodiments, significant homology is 100% sequence complementarity. In some embodiments, significant homology is 50% or greater sequence complementarity. In some embodiments, significant homology is 60% or greater sequence complementarity. In some embodiments, significant homology is 70% or greater sequence complementarity. In some embodiments, significant homology is 80% or greater sequence complementarity. In some embodiments, significant homology is 90% or greater sequence complementarity. In some embodiments, significant homology is between 50% and 100% sequence complementarity.

As used herein, the term "contaminant" means an organism similar or identical to constituents of the target population with at least a portion of its genome sharing significant homology with a sequence which is capable of being amplified by the nucleic acid primers used for amplification of the target population. The contaminant may be introduced into the sample containing the target population inadvertently, thereby producing a falsely positive result for the target population.

As used herein, the term "threshold amount" means an amount of target nucleic acid below which no detection occurs. This term may be used throughout interchangeably with the term "limit of detection." For example, the threshold amount may be set to be 10-fold below the lowest level of target possibly present in a sample. Any target present at lower levels may be a contaminant introduced during sample collection, sample transfer or other steps prior to or during testing, and therefore, should not be detected in the assay. The threshold amount can be lower or higher depending on the requirements of the assay.

As used herein, the term "synthetic template" means a synthetic DNA or RNA molecule designed with significant homology to the primer binding sites designed for target population. The regions of primer homology are located optionally, but preferably, at or near the 5' and 3' ends of the signal suppressor. Intervening sequence exists between these regions that can be amplified by the action of DNA or RNA replicating enzymes in an amplification mixture. The synthetic template can be amplified with the target-specific primers, but has a different sequence in the amplified region so its amplified product may be distinguished from that amplified from the target population. The synthetic template may optionally be a single-stranded nucleic acid, double-stranded nucleic acid, a DNA/RNA duplex, or a DNA plasmid. The synthetic template may optionally be synthesized with modified nucleotide bases or modified backbones. Modifications include but are not limited to: biotinylation, particularly at the 5' end of an oligonucleotide or primer, with or without a spacer or linker, such as the 5-BIOTEG molecule available from IDT Technologies; substitution of ribose-bearing bases in place of deoxyribose-bearing bases in molecules which otherwise consist completely or mostly of DNA bases; and inclusion of one or more phosphoramidite spacers, particularly at the 5' end or the 3' end of an oligonucleotide or primer, such as the C3 spacer available from IDT Technologies. Additional modifications include backbone, sugar, or nucleotide base modifications that increase nucleic acid stability, alter nucleic acid thermal melting, or alter nucleic acid structure. Synthetic templates are a preferred embodiment for use as signal suppressors in direct detection assays as well.

The terms "substantially" or "about" used herein with reference to a quantity includes variations in the recited quantity that are equivalent to the quantity recited, such as an amount that is equivalent to the quantity recited for an intended purpose or function.

As used herein, "amplification mixture" defines the constituents required for amplification of a nucleic acid sequence. These constituents differ with respect to buffer conditions, accessory proteins, or DNA amplifying enzymes, but all must contain minimally target-specific DNA primers, buffers, dNTPs including modified dNTPs such as allylamino-dUTP, and a DNA replicating or amplifying enzyme.

As used herein, "culture" defines a condition that allows for pathogens to grow or replicate. These conditions include incubation in a culture medium such as a broth or on a solid agar. These conditions can also include incubation in bodily fluids such as blood or mucus or potentially growth promoting sites such as the lungs, nares, bloodstream, or gastrointestinal tract. Incubation can occur either in vitro or in vivo.

As used herein, "viable" defines an organism or particle such as a virus that is capable of growing or replicating.

As used herein, "PCR efficiency" is a measure of actual amplicon produced per PCR cycle or round of amplification. PCR efficiency can be understood by the relation, $x^n$, wherein "x" defines efficiency and "n" is the number of PCR cycles. For a perfectly efficient PCR reaction, x=2.

DETAILED DESCRIPTION

Methods, materials, and kits for distinguishing viable or actively growing cells or organisms from non-viable or non-dividing organisms in a clinical sample that optionally has undergone a subsequent step of growth in a culture medium are described herein. The methods and kits may be used to determine if a population detected in a clinical specimen is truly present in the clinical specimen or is an environmental contaminant. For example, a method or kit can be used to determine if bacterial species detected from a positive blood culture aliquot actually was actively cultured in the blood culture bottle or was introduced during subsequent testing.

In one embodiment, the method or kit can be used to determine if a pathogen in a clinical sample is viable or actively growing and, therefore, potentially disease-causing. For example, a non-viable population present in a blood culture bottle would likely exist at a level significantly lower than the lowest level present with a viable population after the culture period. As another example, detection of *Bortedella pertussis* in respiratory samples can be falsely positive if low levels of the pathogen are present in the environment. This can occur due to the presence of *Bortedella pertussis* vaccine, containing dead cells, in the environment.

In another embodiment, the method or kit can be used to determine if a pathogen is present at levels that are associated with disease. For example, *Gardnerella vaginalis* colonizes the anovaginal region of many healthy women, but not until population levels get too high does bacterial vaginosis result.

In another embodiment, the method or kit can be used to determine if a pathogen is truly present in a clinical specimen or was introduced during sampling or testing. For example, persistent carriage of the nares with *Staphylococcus aureus* is associated with detection of >100 colony forming units (CFU) within a patient nasal swab specimen. Lower levels are potentially indicative of intermittent colonization but may also indicate sample or test contamination by the environment.

Many target populations are suitable for detection with the methods, materials, and kits described herein including *Acinetobacter baumannii*; *Actinomyces*, including *Actinomyces israelii*, *Actinomyces gerencseriae*, and *Proprionibacterium propionicus*; *Anaplasma* including *Anaplasma phagocytophilum*; *Bacillus*, including *Bacillus anthracis* and *Bacillus cereus*; *Arcanobacterium* including *Arcanobacterium haemolyticum*; *Bacteroides*; *Borrelia*; *Brucella*; *Burkholderia* including *Burkholderia cepacia* and *Burkholderia pseudomalli*; *Mycobacterium* including *Mycobacterium ulcerans*, *Mycobacterium leprae*, and *Mycobacterium lepromatosis*; *Enterobacteriaceae*; *Enterococcus*; *Campylobacter*; *Bartonella* including *Bartonella henselae*; *Streptococcus* including *Streptococcus pneumoniae*, *Streptococcus pyogenes*, and *Streptococcus agalactiae*; *Haemophilus* including *Haemophilus ducreyi* and *Haemophilus influenzae*; *Chlamydia* including *Chlamydia trachomatis*; *Chlamydophila* including *Chlamydophila pneumonia* and *Chlamydophila trachomatis*; *Vibrio* including *Vibrio cholera*; *Clostridium* including *Clostridium difficile*, *Clostridium botulinum*, and *Clostridium perfringens*; *Corynebacterium* including *Corynebacterium diphtheriae*; *Rickettsia* including *Rickettsia prowazekii*, *Rickettsia akari*, *Rickettsia rickettsii*, and *Rickettsia typhi*; *Ehrlichia* including *Ehrlichia ewingii* and *Ehrlichia chaffeensis*; *Fusobacterium*; *Neisseria* including *Neisseria gonorrhoeae* and *Neisseria meningitidis*; *Klebsiella* including *Klebsiella granulomatis*; *Helicobacter* including *Helicobacter pylori*; *Kingella* including *Kingella kingae*; *Legionella* including *Legionella pneumophila*; *Nocardia*; *Bordetella* including *Bordetella pertussis*; *Listeria* including *Listeria monocytogenes*; *Shigella*; *Salmonella*; *Campylobacter* including *Campylobacter coli* and *Campylobacter jejuni*; and *Yersinia* including *Yersinia pseudotuberculosis*, *Yersinia enterolitica*, and *Yersinia pestis*.

Fungi, yeasts, molds, and similar populations can also be detected using these methods, materials, and kits. These include but are not limited to organisms of the genera *Aspergillus*, *Piedraia*, *Blastomyces*, *Candida*, *Fonsecaea*, *Coccidioides*, *Cryptococcus*, *Geotrichum*, *Microsporidia*, *Malassezia*, and *Trichosporon*.

Other organisms, viruses, cell lines, and cell types may also be detected using the materials, methods, and kits described herein. Populations of eukaryotic cells (cultured, isolated, or growing in their natural state) such as cancer cells serve as additional examples. Unicellular eukaryotes and multicellular eukaryotes (fungal, plant, or animal) can also be targets. These types of cells and organisms can also function as signal suppressors. In addition, cells may be cultured in a growth medium or in the sample in order to increase the number of detectable cells or organisms present. The culturing step would occur between the step of isolating the sample and amplifying the nucleic acid.

Many sample types are suitable for detection with the methods, materials, and kits described herein. These include a variety of culture media such as blood culture including those which are formulated to bind growth inhibitors such as antibiotics. Additionally laboratory methods such as incubation in broth cultures such as McConkey broth, and solid agar cultures such as blood agar or chocolate agar are attractive sample types. Other sample types include sterile fluids such as cerebrospinal (CSF), urine and blood. Other bodily fluids can serve as potential sample types including mucus, nasal aspirates, lung biopsies, lung aspirates, and feces. Swabs such as nasal, vaginal, and rectal are further specimen types.

In general, environmental or reagent contamination occurs at low absolute quantity of organism (for instance, about 100 or fewer colony-forming units (CFU) in a sample). Therefore, the present methods and kits identified herein use a "signal suppressor" approach to threshold detection of low levels of organism, eliminating detection of low level environmental or reagent contamination. The signal suppressor approach works by adding a non-target organism or synthetic nucleic acid template as a signal suppressor to a reaction in which a target population of interest, optionally previously subjected to growth inducing conditions such as in broth or blood culture or bodily fluids such as mucus or blood, is subjected to nucleic acid amplification reactions for subsequent detection. The signal suppressor is added at a level that will eliminate the detection of amplification of target populations (including contaminant populations with significant homology to the primer sequences) present below the lower threshold of detection of the target population. The signal suppressor has sufficient homology to the primer sequences used to amplify target sequences to compete with the target for amplification. Levels of signal suppressor can be determined based on knowledge of the relative amplification rate compared with the target population, the limit of detection of the detection method, and the concentration of DNA primers used in the amplification reaction.

In one embodiment, the signal suppressor is used in an assay intended for direct detection of target sequences by hybridization, with no need for nucleic acid amplification. In this approach, a nucleic acid sequence with homology to the target probe(s) is added as a signal suppressor to a sample that may contain the target sequence/organism. The signal suppressor is added at a level such that the limit of detection is adjusted to not detect below the presumed lowest possible level of target organism present in the sample. For example, detection of pathogens which cause bacterial vaginosis (BV) requires threshold levels of >$10^8$ DNA copies/mL for *Atopobium vaginae* and >$10^9$ DNA copies/mL for *Gardnerella vaginalis* to distinguish disease-causing levels of pathogen from those levels that are too low to cause disease. The limit of detection for the Great Basin Portrait is as low as ~$2\times10^6$ DNA copies/mL, making detection of BV causing pathogens attractive for a direct detection assay requiring no target amplification reaction. Signal suppression, however, would be needed to create an accurate test for diagnosing levels of pathogen that cause BV.

In another embodiment, a synthetic template can be designed as a signal suppressor with homology to the target-specific primers. A synthetic template may be used with any embodiment, and particularly if there is no suitable non-target species available.

The signal suppressor can have a region of 100% homology with the primers used to amplify the target, but optionally can have less than 100% homology. The degree of homology required is determined by the relative amplification rate compared to the target population. If the rate is too low, suppression cannot occur.

Two primers make up a primer pair. An upstream primer anneals to an upstream annealing site on the nucleic acid to be amplified, and a downstream primer anneals to a downstream annealing site. In a nucleic acid amplification reaction, the primers are used as a starting point for DNA synthesis, and a polymerase amplifies a DNA sequence between the upstream and the downstream annealing sites.

One use for these methods and kits is a test designed to amplify variable regions within a gene that can be used to identify *Staphylococcus* to the species level. Such a test can be used to distinguish, for example, a target methicillin-resistant *Staphylococcus aureus* (MRSA) species (or other clinically relevant species) from a non-target (non-pathogenic) *Staphylococcal* species.

In one embodiment, a method for such testing includes providing a specimen containing a target population, adding a signal suppressor to the specimen in a quantity sufficient to impose a limit of detection, amplifying at least one nucleic acid from the specimen using an amplification mixture, and detecting a signal specific to the target population.

In one example of such a method, a blood sample containing *Staphylococcus* species, such as MRSA or methicillin-sensitive *Staphylococcus aureus* (MSSA) is provided. This sample is then mixed with a signal suppressor organism, for example *Staphylococcus succinus* or *Staphylococcus muscae* (which are *Staphylococcal* species very rarely present in human blood and have not been shown to cause infections of the bloodstream), in a predetermined amount. The resulting mixture is then subjected to conditions to lyse the cells thereby exposing DNA targets. Next, amplification reagents including DNA polymerase, buffers, dNTPs, and biotinylated target-specific primers for PCR are added and a DNA target amplification reaction is initiated by thermal cycling the sample. Following the amplification step, the sample is added to a hybridization buffer and then incubated on a chip surface. Attached to the chip surface is an array of target-specific DNA capture probes to which amplified target sequences in the sample can hybridize. After washing away un-hybridized materials, the biotin present on amplified target (due to the incorporation via the biotin-labeled primer) is detected by binding to an anti-biotin antibody conjugated to the enzyme horse radish peroxidase (anti-biotin/HRP). Following a wash step to remove anti-biotin/HRP, the chip is incubated with a precipitating formulation of the substrate TMB. The product of the reaction between TMB and anti-biotin/HRP creates a colored spot on the surface which can then be detected by the naked eye or a digital, CMOS, or CCD camera.

Any suitable nucleic acid amplification technique variant or combination of techniques may be used in accordance with the detection protocol. These include isothermal amplification methods including but not limited to helicase-dependent amplification (HDA), loop-mediated amplification (LAMP), nicking enzyme amplification reactions (NEAR), and recombinase polymerase amplification (RPA) can be used. Moreover, variable-temperature techniques may also be employed. These include, but are not limited to, multiplex PCR, asymmetric PCR, long PCR, nested PCR, quantitative PCR, hot-start PCR, touchdown PCR, assembly PCR, ligation-mediated PCR, inverse PCR, and thermal asymmetric interlaced PCR. If either the target population or the signal suppressor has an RNA template, a reverse transcription step may be employed prior to amplification. This could also include RNA copying or amplifying reaction such as transcription-mediated amplification (TMA) or nucleic acid sequence based amplification (NASBA).

Any suitable polymerase or combination of polymerases may be used in the amplification reaction. These include but are not limited to Klenow fragment, T4 DNA polymerase, Taq polymerase, Stoffel fragment, Pfu polymerase, Vent (*Thermococcus litoralis*) polymerase, Gst polymerase, Bst polymerase, Pwo polymerase, Tth polymerase, T7 RNA polymerase, and variations of these and other polymerases that have been developed.

Other methods of detection may be employed without departing from the scope of the present reaction. For instance, rather than a peroxidase-conjugated antibody, one may substitute an alkaline phosphatase and the appropriate substrate. Alternatively, fluorescently-tagged antibody might be used, or an enzyme that catalyzes a fluorogenic or chemiluminescent reaction by be substituted. Alternately, an avidin variant, such as streptavidin or neutravidin, may be used in place of an antibody for binding biotin. Biotin may also be detected by incubation with 2-(4-hydroxyazobenzene) benzoic acid (HABA) and measuring the absorbance change.

A molecule other than biotin may be used to label the probing oligonucleotide, and its conjugate molecule substituted in the detection step. The oligonucleotide may itself be labeled with a fluorescent molecule. Further techniques for visualizing include fluorescent resonance energy transfer and incorporation of intercalating molecules such as ethidium bromide. Fluorescent nucleotides may also be incorporated into the reaction mixture, such as deoxyuridine triphosphate (dUTP) coupled with a fluorophore such as fluorescein, rhodamine, eosin, cyanine, BODIPY and ALEXA fluors, and the like.

Other solid supports may be used for solid support-based detection including glass slides, latex, polystyrene, or silicon dioxide beads including microspheres, or microtiter plates.

Further, detection of fluorescent signals produced during real-time PCR may be employed. In this approach a suppressor is added to the reaction with complementarity to target nucleic acids that overlap target-specific DNA primers. The suppressor will have a different sequence between the primer binding regions than the target nucleic acid. Target-specific probes (such as Taq Man probes) which produce fluorescent signal upon binding are not active to bind to amplified suppressor. Levels of suppressor can be set to delay or eliminate detection of low level target nucleic acids that may contaminate the tested sample.

In the development of an assay aimed at the detection of *Staphylococcal* species in blood cultures it was observed that there was a high level (20-40%) of false positive results when negative blood cultures were tested due to contamination of tests from *Staphylococcal* species present in the environment. Quantitative PCR revealed that the levels of environmental contamination were very low, typically 1-3 copies of *staphylococci* per reaction. Following the culturing step, blood cultures that are truly positive for *staphylococci* contain more than 500 to 500,000 CFU of *staphylococci* per 50 microliter reaction. Based on this observation a method was sought that could eliminate detection of low level amounts (<50 CFU or 10-fold below the lowest expected level in a blood culture truly positive for *staphylococci*) of contaminating *staphylococci* while still being able to detect the target sequence of interest at clinically relevant levels. One approach to doing this is to simply amplify for time sufficient such that only >50 CFU present is amplified to detectable levels. However, practically this is impossible to repeatedly perform as potential inhibitors in the sample matrix in clinical samples such as blood or feces makes amplification time quite variable; in some cases even higher levels of *staphylococci* would not be sufficiently amplified whereas in other cases even low levels could be detected.

The presently described techniques and kits enable a repeatable approach for eliminating detection of low level contaminating bacteria in a chip-based or other end point detection assay by consuming the DNA primer present in an amplification reaction with an exogenously introduced sequence (termed signal suppressor herein) before amplification of low level environmental contaminants result in detectable quantities. Nevertheless, an operator must still be able to detect the target sequence of interest at clinically relevant levels, so the level of the signal suppressor must be accurately assessed.

To determine the quantity of exogenous sequence, or signal suppressor, hereafter referred to as (S), to be used, several factors are considered. These include the amount (in number of molecules) of primer included in the amplification reaction specific for each target nucleic acid sequence, hereafter referred to as (P); the lower limit of detection of the detection platform used to detect amplified target DNA sequences, hereafter referred to as (LLOD); the threshold amount in number of copies, hereafter referred to as (Ta); the amplification rate for the suppressor hereafter referred to as $k_1$; and the amplification rate for the target/contaminant nucleic acid sequence(s) hereafter referred to as $k_2$.

Exponential association kinetics govern the rates of amplification for HDA. With the hypothesis that all of the DNA primer (P) needs to be consumed before the contaminating level of organism (e.g. *staphylococci*) present below a threshold amount (Ta) is amplified to detectable level (LOD), the following relations are identified in which t represents a unit of time:

$$(P) = (S) \times e^{k_1 t} \quad \text{Relation (1)}$$

$$(LLOD) = (Ta) \times e^{k_2 t} \quad \text{Relation (2)}$$

To identify the amount of suppressor to use, the ratio of relation (1) to relation (2) is compared. This amount can be calculated by equation (1) below:

$$(S) = \frac{(P \times Ta \times e^{k_2 t - k_1 t})}{LLOD} \quad \text{Equation (1)}$$

In an embodiment in which the signal suppressor and the target population/contaminant have the same amplification rate, the equation is simplified:

$$(S) = \left(\frac{P \times Ta}{LLOD}\right) \quad \text{Equation (2)}$$

For a PCR method, equation (1) is replaced by equation (3) below where (x) is the PCR efficiency for the suppressor, (y) is the PCR efficiency for the target/contaminant, and (n) is the number of PCR cycles run in the amplification reaction.

$$(S) = \left(\frac{P \times Ta \times y^n}{LLOD \times x^n}\right) \quad \text{Equation (3)}$$

In an embodiment in which there is equal amplification efficiency for both the signal suppressor and the target population, the equation simplifies to Equation (2) above.

As a practical guide to determine the amount of suppressor required to eliminate the detection of target sequences below a threshold, the following is determined. First, the primer amount used in the amplification reaction is determined. For example, use of 100 nM primer in an amplification reaction equates to $3 \times 10^{12}$ copies in a 50 L reaction.

Next, the detection system LLOD is determined. LLOD can be determined by a titration experiment with labeled target sequences. LLOD is defined as the lowest amount of target sequence that is detectable above background. In the case of the chip used in examples described hereafter, the LLOD is $3 \times 10^8$ copies under experimental conditions utilized. It is understood that changes in time, temperature, and concentration of reagents can have an impact on the LLOD in many systems.

Next, amplification rate of the suppressor (isothermal amplification) or PCR efficiency for the suppressor is determined. To determine amplification rate, a titration of the suppressor is subjected to a real-time amplification assay.

In the case of isothermal amplification, amplification rate is expressed as the reciprocal of doubling time. Doubling time is calculated from linear regression of a plot of ln (suppressor input) versus crossing point (Cp), where the doubling time ($t_d$) is ln2/slope. Amplification rate is ($1/t_d$).

In the case of PCR efficiency, amplification rate is calculated by plotting log (suppressor input) versus Cp. The slope of the line is the negative reciprocal of the log of efficiency.

Next, amplification rate (isothermal amplification) or PCR efficiency of the target/contaminant sequence is determined. This is determined using the same approach as determining amplification rate of the suppressor.

Next, the desired threshold is found. This level depends on the level of target sequence to be tested. For example in positive blood cultures (wherein organisms present in a blood sample are subject to a culture step in blood culture media bottles), the level of *staphylococci* present in alarm positive samples occurs in a range of $1 \times 10^6$-$1 \times 10^9$ CFU/mL. If the sample is diluted 100-fold to reduce effect of amplification inhibitors, sample is 10,000-10,000,000 CFU/mL. In a typical amplification reaction of 50 uL this equates to 500-500,000 CFU/reaction. So in this example, a threshold value 10-fold below the lowest possible amount of *staphylococci* present in a positive blood culture would be 50 CFU. Because we have typically observed contaminating levels 1-3 CFU of *Staphylococci* in the environment, this threshold provides a very tolerant level to distinguish truly positive blood cultures from environmental contaminants. While, in this example, a threshold of 50 CFU is utilized, the threshold level can be adjusted for each application. In the instance of nasal swab screening for *Staphylococcus aureus*, a threshold level of lower amounts such as 5 CFU and even 1-3 CFU may be employed. In one embodiment, detection of such a level of *Staphylococcus* from a nasal swab includes the use of the femB-F6 primer (SEQ. ID NO. 19) with a biotin tag such as the 5BioTEG at its 5' end as a forward primer, and femB-R4 (SEQ. ID. NO. 20) as a reverse primer. In this context, a signal suppressor such as FemBSyn1 (SEQ. ID NO. 22) can be used to assist in distinguishing a positive sample from one having a contaminant. Detection may in part utilize the capture probe femB-CP2 (SEQ. ID NO. 21), which may optionally be immobilized on a surface and tethered to said surface using any suitable linker and/or spacer molecule or DNA sequence.

As an additional example for detection of *Bortedella pertussis* in clinical respiratory samples a threshold of 100-500 CFU/mL may be employed to sensitively detect the true presence of the pathogen in the sample versus an environmental contaminant from vaccine present in the laboratory that could be introduced during testing.

Next, amplification time (isothermal amplification) or cycle number (PCR) required for the threshold amount to be amplified to detectable levels is found. This value is the most accurate method for determining the levels of signal suppressor required to consume all primers before a target/contaminant is amplified to detectable levels. Arbitrary use of time values will under- or overestimate the amount of signal suppressor required.

In the case wherein the amplification rate (isothermal amplification) or PCR efficiency for both the signal suppressor and target/contaminant sequences are the same this factor does not matter and the amount of suppressor required can be calculated by Equation (1).

In the case wherein the amplification rate (isothermal amplification) is unequal hod is the amplification time required for target/contaminant amplicon quantities to reach chip limits of detection as defined by the relationship:

$$t_{(llod)} = (\ln(LLOD) - \ln(Ta)) \div k_1 \quad \text{Equation (4)}$$

where $k_1$ is the amplification rate for target/contaminant amplicon.

In the case where the PCR efficiency is unequal, $n_{lod}$ is the cycle number required for contaminant amplicon to reach chip limits of detection as defined by the relationship:

$$n_{llod} = -\left(\frac{1}{\log}(X)\right) \times \log(Ta) + (\log(LLOD)/\log(X)) \quad \text{Equation (5)}$$

where X is the PCR efficiency for target/contaminant amplicon.

With all of the above variables defined, the user can then input the information into Equation (2) for the instance wherein the amplification rate or PCR efficiency is identical. When amplification rates are different in isothermal reaction all of the defined variables from 1-6 above can be input into Equation (1) wherein $t_{lod}$ is substituted for t. When PCR efficiencies are different in PCR reactions all of the defined variables from 1-6 above can be input into Equation (3) wherein $n_{lod}$ is substituted for n.

It should be appreciated that even if the signal suppressor and the target population or contaminant population each have complete homology to the DNA primer, that does not mean that they will have equal amplification efficiency. Other factors may create rate differences, including cell lysis efficiency, nucleic acid secondary and potentially tertiary structure affecting amplification speed or primer binding, the guanine and cytosine (GC) content of the target or signal suppressor sequence, and whether the target or signal suppressor are single-stranded, double-stranded or circular.

In one embodiment, when there is mismatching between the primers and the signal suppressor, amplification of the signal suppressor relative to the target/contaminant may be slower requiring greater amounts of signal suppressor. For example, if the amplification rate in HDA reactions for the target organism is 0.9 min$^{-1}$, and the amplification rate for the suppressor is 0.55 min$^{-1}$, the number of signal suppressor cells (when the signal suppressor is an organism or cells) required to eliminate detection below 50 CFU is increased from 5,000 (when amplification rates were identical to the target organism) to greater than 10 million CFU (FIG. 1). It can be appreciated from this example that there exists a practical limit to the allowable differences in rate between the signal suppressor and the target population because at some point the quantity of signal suppressor becomes impractically large.

When synthetic oligonucleotides are used as signal suppressors there are several design elements that must be considered, including the structure and content of the construct. In one embodiment, the synthetic suppressor must contain sequence regions on or near both the 5' and 3' ends that share homology with the primer region of the target gene in order to control the amplification of the target. In another embodiment, a single synthetic template can be designed to control the amplification of multiple target genes through several means, including: the use of unique target gene priming regions on each end (for example the 5' end of the construct is homologous to a geneA primer while the 3' end of the same construct is homologous to a geneB primer), or multiple primer sequences can be built into the 5' and 3' ends of the synthetic template construct in tandem (for example sequences complementary to primers for geneA and geneB are placed in tandem at both the 5' and 3' end of the construct thus generating two unique amplified products from the same construct with both amplified products sharing substantially the same internal sequence). Alternatively, a single construct can be designed such that two or more primer pair regions from two or more unique genes could be amplified with each amplification event resulting in a unique amplified product, thus allowing for the simultaneous suppression and reporting of multiple suppressor events from a single construct. Alternatively, multiple synthetic constructs, each designed to specifically suppress a single target, can be used in combination.

In addition, when synthetic oligonucleotide construct are used as signal suppressors the homology of priming region(s) between the target and signal suppressor construct must be considered. The percentage of homology between the priming regions of the target sequence and the signal suppressor can be as high as 100% or as low as theoretically allowed to still generate an amplification rate sufficient to allow the synthetic template to act as a suppressor. Nucleotide mis-matches can be introduced into the primer regions as necessary at both or either ends of the synthetic construct to control the amplification of the synthetic template relative to the target. The number of mismatches per primer region, as well as the proximity of the mismatches to the 3'end of the primer region will have the largest effect on amplification efficiency of the construct.

In addition, when synthetic oligonucleotide construct are used as signal suppressors, design of the signal suppressor amplified product sequence must be carefully considered. The synthetic construct must contain a unique region that upon amplification can be specifically distinguished from sequences generated via amplification of target(s). This can be achieved through many means including but not limited to: introducing a unique gene sequence from an unrelated gene within the same species; utilizing the same, related or unrelated gene sequence from a different species; utilizing the homologous, related or unrelated gene sequence from a different pathogenic or non-pathogenic organism; exploiting a partially or completely artificial sequence; or utilizing the same intervening sequence that is found in the target but introducing sufficient point mutations such that amplicon generated from the suppressor is detectable uniquely from target amplicon. All synthetic construct should be subjected to BLAST (http://blast.ncbi.nlm.nih.gov/) search to ensure that synthetic sequence(s) will not generate any interference with the assay for all the target genes (both target amplification and probe hybridization).

In addition, when synthetic nucleotide construct are used as signal suppressors physical properties of the constructs must be carefully considered. The length and percentage of GC-content (% GC) are factors that affect amplification efficiency and can be used to control rate of amplification and thus strength of the signal suppressors. In a preferred embodiment, synthetic signal suppressors will be designed to generate amplified products within the size (+/−25%) and GC-content (+/−5%) range of the target amplified product(s).

Numerous devices, kits, and methods may be derived from such teachings. In one aspect, what is provided is a kit for determining whether a sample contains a threshold amount of a target cell. The kit includes a signal suppressor comprising a nucleic acid having a 5' end and a 3' end; an upstream DNA primer for annealing to a nucleic acid of the suppressor at an upstream annealing site; and a downstream DNA primer for annealing to a nucleic acid of the suppressor at a downstream annealing site; wherein the upstream DNA primer is capable of annealing to a nucleic acid of the target cell at an upstream annealing site and the downstream DNA primer is capable of annealing to a nucleic acid of the target cell at a downstream annealing site, the upstream DNA primer and downstream DNA primer having such sequence that subjecting the sample to a nucleic acid amplification process will cause the upstream DNA primer and the downstream DNA primer to amplify an intervening sequence both of the target cell nucleic acid and the signal suppressor located between the upstream annealing site and the downstream annealing site, and wherein the signal suppressor is provided in sufficient quantity to eliminate detectable levels of amplification of nucleic acid from the target cell if the target cell is present below the threshold amount.

In another aspect, a method of determining whether a sample contains a threshold amount of a target cell population is provided. In a first step, the method includes identifying at least one type of target cell to detect. In a second step, the method includes identifying a limit of detection above which amplification of a nucleic acid from the target cell is noncontaminating. In a third step, the method includes adding at least one signal suppressor nucleic acid for each potential cell type to the sample in a quantity sufficient to ensure that amplification of each potential cell type will not proceed to detectable levels if present below said limit of detection. In a fourth step, the method includes subjecting the sample to a nucleic acid amplification protocol using an amplification mixture comprising a DNA polymerase, a deoxyribonucleotide triphosphate mixture (dNTPs), and at least one pair of DNA primers, each of the pair of DNA primers having a sequence which anneals to a signal suppressor nucleic acid and a nucleic acid of the target cell. In a fifth step, the method includes detecting a signal from the product of the nucleic acid amplification protocol to determine whether the target cell type is present in clinically significant quantities.

In another aspect, a method of determining whether a sample contains at least 500 colony forming units per milliliter of *Staphylococcus* is described. In a first step, the method includes providing a sample to be tested for *Staphylococcus*. In a second step, the method includes adding at least one signal suppressor nucleic acid to the sample in a quantity sufficient to ensure that amplification of a nucleic acid from *Staphylococcus* will not proceed to detectable levels unless at least 500 colony forming units per milliliter. In a third step, the method includes subjecting the sample to a nucleic acid amplification protocol using an amplification mixture comprising a DNA polymerase, a deoxyribonucleotide triphosphate mixture, and at least one pair of DNA primers, each of the pair of DNA primers having a sequence which anneals to a signal suppressor nucleic acid and a nucleic acid of the target cell. In a fourth step, the method includes detecting a signal from the product of the nucleic acid amplification protocol to determine whether at least 500 colony forming units of *Staphylococcus* are present.

In a further aspect, a method of distinguishing one or more viable, proliferating target populations from one or more non-viable or non-proliferating populations comprising providing a specimen containing a target population; adding a signal suppressor to the specimen in a quantity sufficient to impose a limit of detection or threshold amount; amplifying at least one specific nucleic acid target sequence from the specimen using an amplification mixture; and detecting a signal specific to the target population is provided.

In another aspect, a method of distinguishing one or more viable, proliferating target populations from one or more non-viable or non-proliferating populations comprising: providing a specimen containing a target population; culturing the target population in a growth medium; adding a signal suppressor to the specimen in a quantity sufficient to impose a limit of detection or threshold amount; amplifying at least one specific nucleic acid target sequence from the specimen using an amplification mixture having at least one target-specific DNA primer set; and detecting a signal specific to the target population using one or more oligonucleotide probes having sequence homology to the sequence amplified in the target population.

In another aspect, a method of distinguishing one or more target populations from one or more contaminating populations comprising providing a specimen containing a target population; adding a signal suppressor to the specimen in a quantity sufficient to impose a limit of detection or threshold amount; amplifying at least one specific nucleic acid target sequence from the specimen using an amplification mixture; and detecting a signal specific to the target population is provided.

In another aspect, a method of distinguishing one or more viable, proliferating target populations from one or more contaminating populations comprising: providing a specimen containing a target population; culturing the target population in a growth medium; adding a signal suppressor to the specimen in a quantity sufficient to impose a limit of detection or threshold amount; amplifying at least one specific nucleic acid target sequence from the specimen using an amplification mixture having at least one target-specific DNA primer set; and detecting a signal specific to the target population using one or more oligonucleotide probes having sequence homology to the sequence amplified in the target population.

In another aspect, a method of distinguishing one or more target populations causing disease from one or more contaminating or colonizing populations comprising providing a specimen containing a target population; adding a signal suppressor to the specimen in a quantity sufficient to impose a limit of detection or threshold amount; amplifying at least one specific nucleic acid target sequence from the specimen using an amplification mixture; and detecting a signal specific to the target population is provided.

In another aspect, a method of distinguishing one or more target populations causing disease from one or more contaminating or colonizing populations comprising: providing a specimen containing a target population; culturing the target population in a growth medium; adding a signal suppressor to the specimen in a quantity sufficient to impose a limit of detection or threshold amount; amplifying at least one specific nucleic acid target sequence from the specimen using an amplification mixture having at least one target-specific DNA primer set; and detecting a signal specific to the target population using one or more oligonucleotide probes having sequence homology to the sequence amplified in the target population.

In another aspect, a kit is provided for distinguishing one or more viable, proliferating target populations from one or more non-viable or non-proliferating populations comprising: a nucleic acid amplification mixture for amplifying a target DNA sequence, a signal suppressor, and a detection mixture.

In another aspect, a kit is provided for distinguishing one or more target populations from one or more contaminating populations comprising: a nucleic acid amplification mixture for amplifying a target DNA sequence, a signal suppressor, and a detection mixture.

In another aspect, a kit is provided for distinguishing one or more target populations causing disease from one or more contaminating or colonizing populations comprising: a nucleic acid amplification mixture for amplifying a target DNA sequence, a signal suppressor, and a detection mixture.

In another aspect, a kit is provided for distinguishing one or more target populations from one or more contaminating populations comprising: a nucleic acid amplification mixture containing buffers, DNA polymerase, dNTPs, and biotin-labeled DNA primer sets for amplifying a three target DNA sequences: a conserved region of the nuc gene, to identify *Staphylococcus aureus*; a variable region of the tuf gene, to identify various other *Staphylococcal* species; and a conserved region of the gene mecA to detect resistance to oxacillin in the tested *Staphylococcal* species; three signal suppressors each specific to the nuc, tuf, and mecA genes; and a detection chips containing an array of probes used to detect amplified products of the *Staphylococcal* species including *Staphylococcal aureus* and the mecA gene.

EXAMPLES

Example 1

An HDA Amplification/Chip-Based Detection Assay for *Staphylococcal* Species

For the amplification step, 2 L of blood sample can be mixed with 18 L of extraction buffer (Great Basin Scientific). This buffer constitutes an exemplary extraction condition and a variety of buffers at a variety of pH, and different salts, detergents, lysis enzymes, and other additives may be suited to this application.

The sample can then be incubated at about room temperature for about 10 minutes, then heated to about 95° C. for about 3 minutes. Then 4 L of the crude lysate is added to about 36 L of dilution buffer (20 mM Tris-HCl [pH8.8], 10 mM KCl, 7.7 mM $MgSO_4$, 40 mM NaCl, 5 mg/mL bovine serum albumin [BSA], 0.02% Tween-20) containing appropriately diluted synthetic DNA template (suppressor) signal suppressor when necessary and mixed thoroughly. The lysis buffer composition is exemplary and other buffers, salts, additives, and detergents may be suitable. When intact organisms such as *Staphylococcus succinus* or *Staphylococcus muscae* are used as suppressors, they are added during the extraction step at appropriate quantities of cells.

20 L of the extracted and diluted sample are mixed with 20 L of HDA mixture (20 mM Tris-HCl [pH8.8], 40 mM NaCl, 17 mM KCl, 2× enhancer mixture (Great Basin Scientific), 0.8 mM each of dCTP, dGTP and dTTP, 6.8 mM of dATP, 2× EvaGreen (Biotium), 10 ng/L uvrD helicase (BioHelix), 1.6 U/L of Gst DNA polymerase (BioHelix), and 4 ng/L ET SSB, 2×RNase H2 (Great Basin)). Primers are used to amplify conserved sequence within the methicillin-resistance determining gene, mecA, and to amplify a variable region within the *Staphylococcal* tuf gene for identity of various *Staphylococcal* species. Primers in a helicase-dependent amplification can be designed to have a "blocker," or a base which has a ribose sugar instead of a deoxyribose, in order to suppress non-specific amplification at sub-optimal temperatures. Ideally, all primers used have such a base. When amplification is initiated, an RNase which recognizes the modified nucleotide cleaves at the site of the modified base if the primer is annealed to the cognate target nucleic acid sequence or suppressor at elevated temperature. Primers used are 200 nM of mecAf1145 primer (SEQ ID NO. 6, optionally substituting riboadenosine for deoxyriboadenosine at position 27, optionally terminating at its 3' end with at least one iSPC3 phosporamidite), 300 nM of mecAr1244 primer (SEQ ID NO. 7, optionally biotinylated at its 5' end, optionally substituting riboadenosine for deoxyriboadenosine at position 33, optionally terminating at its 3' end with at least one iSPC3 phosporamidite), 400 nM of tuf430L primer (SEQ ID NO. 8, optionally biotinylated at its 5' end, optionally substituting riboadenosine for deoxyriboadenosine at position 33, optionally terminating at its 3' end with at least one iSPC3 phosporamidite) or tuf426f11 primer (SEQ ID NO. 9, optionally substituting riboguanosine for deoxyriboguanosine at position 30, optionally terminating at its 3' end with at least one iSPC3 phosporamidite), and 600 nM of tuf527v1 primer (SEQ ID NO. 10, optionally biotinylated at its 5' end, optionally substituting riboadenosine for deoxyriboadenosine at position 29, optionally terminating at its 3' end with at least one iSPC3 phosporamidite). The reaction mixture is run on Roche Lightcycler480 or a Great Basin Portrait device for card assay for 50 min at 65° C.

The preceding constitutes an exemplary formulation for an amplification reaction. The buffer, salt, additive, pH, detergent conditions, polymerase, nucleotide concentrations, and other additives may be varied as suited to the particular sample used. Moreover, this method is not restricted to use of isothermal amplification.

In this embodiment, detection includes a step of chip hybridization on a Great Basin Portrait (2441 South 3850 West Salt Lake City, Utah 84120) device for card assay or on bench with a manual chip assay. In the manual assay, the chips are attached to the bottom of the wells of a 96-well plate and covered with a microplate sealer. The plate is pre-warmed on a heater block at about 53° C. in an incubator oven for 5-10 min. 80 L each of the hybridization buffer (5×SSC, 5% Blockaid (Great Basin Scientific); 0.05% Tween-20; 0.03% Proclin-30 preservative, and 250 pM biotin-labeled reverse complementary sequences for the hybridization control) is also pre-warmed on a heater block in the 53° C. oven for at least 5 min. 2 L of amplicon is mixed with 18 L of amplicon dilution buffer (20 mM Tris-HCl [pH8.8], 40 mM NaCl, 17 mM KCl; 1x enhancer mixture (Great Basin Scientific); 2.5 mg/mL BSA; 0.01% Tween-20 and 0.01% Triton-100) and heated at 85° C. for 3 min on a PCR machine. Then, 80 L of pre-warmed hybridization buffer is immediately transferred into the PCR tubes (still on the PCR machine), pipetted a few times to mix well, and then transferred onto the pre-warmed chips in the 96-well plate and incubated in the 53° C. oven for 5 min. The chips are washed with 100 L of wash buffer A (0.1×SSC, 0.01% SDS) for 3 times and 100 L of wash buffer B (0.1×SSC, 0.01% Tween-20) for 3 times, and then 100 L of conjugate solution (a peroxidase-conjugated mouse monoclonal antibody against biotin, Jackson ImmunoResearch Laboratory, Inc.) is added onto each chip. After 4 min incubation at room temperature, the conjugate solution is removed and the chips are washed again 3 times with wash buffer B (0.1×SSC, 0.01% Tween-20). Then, 100 L of membrane TMB is added onto each chip and incubated for 2 min at room temperature. Finally, the chips are washed briefly 2 times with water and 2 times with ethanol, respectively. The chips are dried with a stream of nitrogen gas and then an image is taken using CCD camera for each chip.

Figure 2:
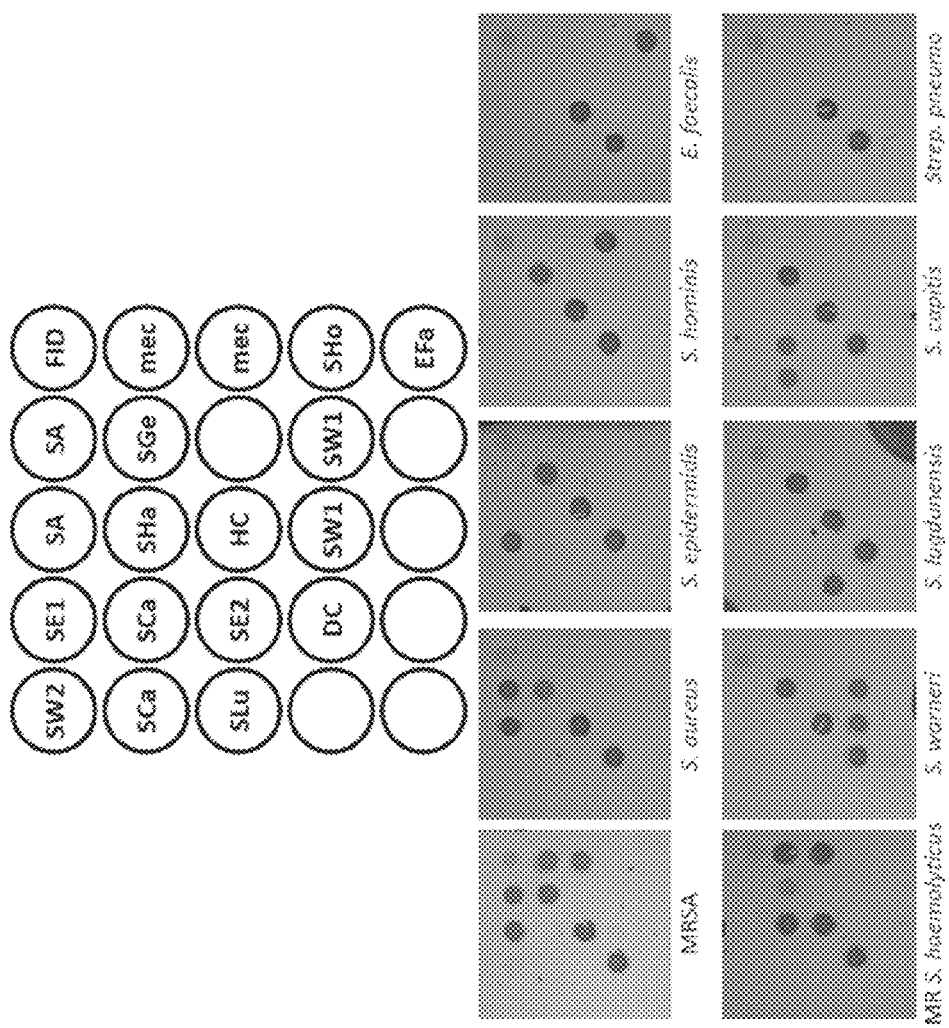
FIG. 2 is a series of images representative of a detection assay in accordance with one aspect of the invention.

Sample CCD image results are seen for this assay in FIG. 2 for the amplification of various bacterial species. Variability within the tuf amplified product can be used to detect various *staphylococci* to the species level by using surface-immobilized probes specific to individual species. Probes which target conserved sequence within the mecA gene can be used to identify *staphylococci* that contain this gene. The various signal patterns from the chip array are used to determine the identity of the bacterial species using the chip map as shown.

Example 2

Effect of HDA Amplification Rates on Suppressor Input Requirements

In this example, various different amplification rates for the Suppressor are inputted into equation (1) using a fixed amplification rate of 0.9/min for the target population to determine how many signal suppressor input copies were required to create a Threshold amount of 50 nucleic acid copies. As is seen in FIG. 1, the amplification rate of the signal Suppressor as compared with the target (or contaminating) organism population has a significant impact on how many signal suppressor copies are required. At equal amplification rates, 5,000 suppressor copies were required, but in the case wherein the amplification rate is 0.45/min or half that of the target amplification rate, more than 10,000,000 Suppressor copies are required.

Example 3

Determination of HDA Amplification Rates for Suppressors

In this example the amplification rate for two potential signal suppressors (*S. succinus* and *S. muscae*) to be used in the Staphylococcal species detection assay described in Example 1 are characterized. In this study, two primers sets that target the tuf gene in *staphylococci* are tested. These gene regions are highly conserved for the genus *staphylococci* allowing for primer binding to most or all of the species of *staphylococci*. Between these conserved regions are highly variable regions that are amplified by the action of DNA polymerase. This variability can be used to determine the species of *staphylococci* present. Each primer set uses the same reverse primer (tuf527v1), but a different forward primer, either tuf430L or tuf426f11. In the example, *S. succinus* has two mismatched nucleotides in the primer flap for the primer tuf430L, whereas *S. muscae* has complete homology. Primer tuf426f11 was created to eliminate the mismatches in *S. succinus*.

A titration of the signal suppressor (3, 10, 30, 100, 300 CFU) is subjected to the amplification reaction conditions described in Example 1 with the reaction performed in a Lightcyler real-time HDA assay for 50 minutes at 65° C. Doubling time is calculated from linear regression of a plot of ln(cell input) versus crossing point (Cp), where doubling time ($t_d$) is ln2/slope. Amplification rate is ($1/t_d$).

Based on the results, the two mismatches in primer tuf430L for *S. succinus* negatively impact amplification rate (0.55/min.). However, with the mismatches eliminated in primer tuf426f11 *S. succinus* has appreciably the same amplification rate as the target population of 0.9/min. *S. muscae*, as expected, has an amplification rate of 0.9/min. using tuf430L primer set. This data shows the amplification rate of the signal suppressor is impacted based on the degree of homology to the primers used.

Example 4

Effect of *S. succinus* Suppressor Input Amounts on LOD for Detection of Methicillin-Sensitive *S. aureus* (MSSA)

In another aspect of the method, modifying the amount of signal suppressor can be used to alter the limit of detection. In an exemplary experiment, different input amounts of *S. succinus* cells (0, 1000, 5000, 425000 and 2,125,000 CFU) are used to determine the impact on the detection of amplified MSSA cells with two different pairs of tuf gene primers (tuf426f11/tuf527v1 and tuf430L/tuf527v1), which have different rates for the amplification of *S. succinus*, but similar rates for the amplification of MSSA (0.9/min.). Each input amount of *S. succinus* is tested against a dose response of known amounts of MSSA (0, 3, 30, 300, 3000 CFU). The reactions are amplified on Roche LightCycler480 at 65° C. for 50 minutes and the limit of detection (LOD) for MSSA is determined by hybridizing the resultant amplicons to the tuf gene probe set spotted on the chip.

In this example, the LOD is observed to be 3 CFU in the absence of signal suppressor. Under conditions where the signal suppressor has a similar amplification rate to the target (MSSA) using primer set of tuf426f11 and tuf527v1, the limit of detection of the assay for MSSA can be increased in a dose dependent manner, with a 10-30 fold effect at 5,000 CFU input suppressor amounts observed, increasing the LOD from 3 CFU to 30-100 CFU. However, when the suppressor has a 40% lower amplification rate using the tuf430L and tuf527v1 primer set, no impact on limit of detection of MSSA is observed with up to 2,125,000 CFU, consistent with predictions made by the mathematical model as illustrated in FIG. 1.

Example 5

Use of Two Synthetic Templates as Independent Sequence-Specific Signal Suppressors In another aspect, a synthetic template may be used as the signal suppressor. In one exemplary study, a fixed amount of the suppressor synthetic template TufSyn2 (SEQ ID NO. 1) (500,000 copies input, determined to worsen LOD by ~30-fold), is used to suppress the tuf gene amplification such that the LOD is 100 CFU. Relatively greater amounts of TufSyn2 are required compared with *S. muscae* likely because Tuf-Syn2 contains two mismatches under the primer binding site for amplification of tuf gene sequence within target population. Additionally in this example, different input amount of the synthetic template, MecSyn3 (SEQ ID NO. 2) (0, 5 k, 50 k and 500 k copies) which also contains two mismatched bases under the primer binding site for amplification of target population, are used to suppress the mecA gene amplification against different amount of MRSA cell input (3, 10, 30, 100 and 300 CFU). The reactions are amplified on a Roche LightCycler480 at 65° C. for 50 minutes and the limit of detection (LOD) for MRSA is determined by hybridizing the resultant amplicons to the tuf and mecA gene probes spotted on the chip.

These results show the ability of two different suppressors to simultaneously and specifically suppress the limit of detection of two separate genes used in the *staphylococci* detection assay. Using a fixed amount of 500,000 suppressor copies to worsen the LOD for the tuf gene to 100 CFU for tuf-specific probes on the chip surface, the effect of a mecA-specific suppressor on the mecA detection can be independently observed. As expected, the mecA suppressor works in a dose dependent manner. No effect on LOD (3 CFU) is observed using up to 5,000 copies of the mecA suppressor, but with 50,000 copies of mecA suppressor the LOD is worsened to 30 CFU (10-fold effect) and to 100 CFU using 500,000 copies of the mecA suppressor. This shows that this approach is sequence-specific in its effect on LOD.

Example 6

Effect of Suppressors on Mitigating Detecting of Contaminating *Staphylococcal* Species in an Assay Designed to Detect *Staphylococcal* Species from Positive Blood Cultures One example of an experiment for determination is described in the following study of environmental contamination by *staphylococci* during testing.

In this study, the synthetic template TufSyn2 (with input of 0, 25,000 or 250,000 copies) is loaded into Great Basin's Portrait cards with blood samples previously determined to be negative for the presence of *staphylococci* and run on the Portrait Analyzer (10 cards each for 0 or 25,000 copies of TufSyn2 input and 29 cards for 250,000 copies of Tufsyn2 input). The reactions are amplified on Portrait at 65° C.

The false positive/contamination rate is determined by the hybridization signal on Portrait with the tuf gene probe set spotted on the chip. Any detectable probe signal is scored as "false positive" because negative blood cultures are used in this study and no signal should be present. If no signal suppressor is present 40% of the tested cards are, in this example, falsely positive for various *Staphylococcal* species. Addition of 25,000 signal suppressor copies reduces the false positive rate to 20% and addition of 250,000 signal suppressor copies completely eliminates false positive detection from environmental contamination.

Example 7

A PCR Amplification/Chip-Based Detection Assay for *Staphylococcal* Species

To lyse cells and release target DNA from cells, a blood culture sample can be diluted 1:10 by volume into extraction buffer solution (Great Basin Scientific). For example, 2 L of blood sample is mixed with 18 L of extraction buffer. The samples are then incubated at ambient temperatures for 10 min followed by a 3 min denaturation at 95° C. Alternatively, the samples are incubated at 80° C. for 8 min followed by a 2 min denaturation at 95° C. The extraction buffers, incubation times and incubation temperatures constitute an exemplary extraction condition. A variety of buffers at a variety of pH, various salts and salt concentrations, detergents, lysis enzymes, and other additives may also be suited to this application.

An aliquot (1 L) of the crude lysate is added to an amplification reaction mixture (49 L) and subjected to subsequent amplification via PCR. The PCR amplification reaction mixture contains: 25 mM Tris-HCl [pH 8.8], 50 mM KCl, 2 mM $MgSO_4$, 3 mg/uL bovine serum albumin [BSA], 0.001% Tween-20, 0.0002% Proclin-300, 0.2-1 mM primers, 0.8 mM dNTPs, 2.5% sucrose, 3.75% Ficoll-70, 2.5% Ficoll-400, 0.005% Triton X-100, Evagreen, 2-4U Hot Start Taq Polymerase, and appropriately diluted synthetic DNA template signal suppressor when necessary. Primers used were as follows: 200 nM of mec-3F primer (SEQ ID NO. 11), 600 nM mec-3RB primer (SEQ ID NO. 12, optionally biotinylated at its 5' end), 150 nM nuc-6F primer (SEQ ID NO. 13), 450 nuc-6RB primer (SEQ ID NO. 14, optionally biotinylated at its 5' end), 150 nM tuf-3F primer (SEQ ID NO. 15) and 450 nM tuf-3RB primer (SEQ ID NO. 16, optionally biotinylated at its 5' end). The reaction mixture is mixed thoroughly and run on either a Roche LightCycler480 or a Great Basin Portrait device for card assay.

The preceding constitutes an exemplary formulation for a PCR-based amplification reaction. The buffer, salt and salt concentrations, additive(s) and additive concentration, pH, detergent conditions, polymerase and polymerase conditions, nucleotide concentrations, and additives may be varied as suited to the particular sample used.

In this embodiment, detection includes a step of chip hybridization on a Great Basin Portrait (2441 South 3850 West Salt Lake City, Utah 84120) device for card assay or on bench for manual chip assay exactly as described in Example 1.

Example 8

Effect of Single-Stranded Synthetic Construct Suppressor Input on Limit of Detection (LOD) of *Staphylococcal* Species from Positive Blood Cultures In one exemplary study, the limit of detection (LOD) of a *Staphylococcus aureus*-specific gene is determined in a PCR-based assay in the absence and presence of a single-stranded Suppressor synthetic construct, NucSyn1 (SEQ ID NO. 3). For this study the nuc gene from a methicillin-susceptible *Staphylococcus aureus* (MSSA) strain was amplified with nuc-1FB (SEQ ID NO. 17, optionally biotinylated at its 5' end) and nuc-1R (SEQ ID NO. 18) primer at various bacterial inputs from positive blood culture. NucSyn1 synthetic template is added to alarm-positive MSSA blood culture samples, loaded into Great Basin's Portrait cards, and run on the device utilizing a PCR-based amplification protocol. With no synthetic template present the LOD for nuc in this strain is in the range of 1-3 CFU/reaction. Upon addition of 100,000 copies of NucSyn1 the LOD is increased to 10 CFU. Finally, when NucSyn1 input of 500,000 copies was tested, the observed LOD of nuc was suppressed to 50 CFU, thereby demonstrating that the LOD of specific gene targets can also be tuned by controlling the concentration of synthetic template within assays utilizing PCR amplification of target sequences.

Example 9

Combined Effect of Multiple Synthetic Signal Suppressors on Detecting Contaminating *Staphylococci* Species from Positive Blood Cultures A study was conducted to determine the baseline environmental contamination rate of *Staphylococcal* species, both methicillin-resistant and methicillin-susceptible, via analysis of cards containing no sample input on the Portrait device (i.e. negative controls), with and without signal suppressor present.

The baseline contamination rate for PCR-mediated *Staphylococcal* species detection is determined by the detection of hybridization signal to either a tuf gene probe, indicating *staphylococci* contamination, and/or a nuc gene probe indicating the contamination with *S. aureus*. For clarification, when present in the reaction *S. aureus* will cause signal on both the tuf and nuc probes, however other common *Staphylococcal* contaminant species, such as *S. epidermidis*, will only cause signal on a tuf probe, thus allowing for specific differentiation and measurement of *S. aureus* contamination rate independent from other *Staphylococcal* species. Any detectable probe signal is scored as "false positive" because empty cards containing no sample input are used in this study and no signal should be present. When cards containing no sample are analyzed with no signal suppressor present, 7/16 or 44% of the cards tested are falsely positive for various *Staphylococcal* species (measured via tuf probe signal). Of these seven false positive cards, one is specifically contaminated with *S. aureus* (measured via signal of nuc probe).

In a follow-up study the baseline contamination rate is challenged through the addition of a single-stranded synthetic DNA construct with complementarity to the tuf gene, TufSyn10 (SEQ ID NO. 4), designed to serve as a signal suppressor for the tuf gene target. A solution of TufSyn10 is loaded onto cards to achieve a final concentration of 1,000,000 copies/L in the amplification reaction. No additional sample is added. At this concentration TufSyn10 is able to completely ameliorate the 40% contamination rate as observed via lack of tuf probe signal in all cards ran (i.e. 0% *Staphylococcal* contamination). However with only TufSyn10, *S. aureus* contamination persists as evidence through signal on the nuc probe in one test.

Therefore in an additional follow-up study, the TufSyn10 construct is combined with a single-stranded synthetic DNA construct designed to suppress nuc gene target signal, NucSyn3 (SEQ ID NO. 5). The two synthetic constructs are used in combination to further challenge the contamination rate. At equimolar inputs of NucSyn3 and TufSyn10 (final concentration of $1 \times 10^6$ copies/L in the amplification reaction) all contaminating signal is suppressed on both the nuc and tuf probes (i.e. 0% contamination). The studies described in this example demonstrate that multiple synthetic templates, designed to target multiple genes, can be successfully used in combination. When multiple synthetic constructs are combined in a single reaction they function completely independently from each other, even when the constructs have inherently different amplification rates. Furthermore, multiple synthetic suppressor constructs of appropriately varied suppressive strength can be used in combination to simultaneously suppress multiple genes to varying degrees.

In another embodiment, a kit is disclosed for carrying out a detection protocol and which is capable of discriminating between viable and non-viable or contaminating populations. Such a kit would include a number of components, including a nucleic acid amplification mixture for amplifying the target DNA sequence, a signal suppressor, and a detection mixture. It could also optionally contain a DNA polymerase, buffers and a dNTP mix. The signal suppressor could be a synthetic nucleic acid. Amplification primers might also be optionally provided in such a kit.

While the above description contains many specifics, those specifics should not be construed as limitations on the scope of the disclosure. Those skilled in the art will envision other possible variations which are within the scope and spirit of the disclosure as defined by the following claims.

The invention claimed is:

1. A method of determining whether a sample contains a threshold amount of a target cell population, comprising:
identifying at least one type of target cell to detect from a sample;
identifying a threshold amount above which amplification of a target nucleic acid from the target cell is noncontaminating;
adding at least one signal suppressor nucleic acid for each type of target cell to the sample in a quantity sufficient to ensure that amplification of the target nucleic acid of each type of target cell will not proceed to detectable levels if the target cell of that type is present in a quantity below the threshold amount;
amplifying the target nucleic acid in an amplification step with a DNA polymerase, a deoxyribonucleotide triphosphate mixture, and at least one pair of DNA primers, each of the pair of DNA primers having a sequence that anneals to a signal suppressor nucleic acid and the target nucleic acid; and
detecting a signal from the product of the amplification step in a detection step, to determine whether the cell type is present in a noncontaminating quantity.

2. The method of claim 1, wherein the amplification step comprises helicase dependent amplification.

3. The method of claim 1, wherein the amplification step comprises polymerase chain reaction.

4. The method of claim 1, wherein the detection step further comprises detecting precipitate from a reaction product catalyzed by horseradish peroxidase activity.

5. The method of claim 1, wherein the target cell comprises a *Staphylococcal* species, and the threshold amount is about 10,000 to about 100,000 colony forming units per milliliter.

6. The method of claim 1, wherein the target cell is a *Staphylococcal* species, and the threshold amount is about 500 colony forming units.

7. The method of claim 1, wherein the sample comprises human blood.

8. The method of claim 1, wherein the DNA primers amplify the target nucleic acid at an amplification rate equal to a rate of signal suppressor amplification; and wherein the quantity of signal suppressor required to achieve a desired threshold amount is the product of a number of primer molecules and a threshold amount divided by a lower limit of detection.

9. The method of claim 1, wherein the DNA primers amplify the target nucleic acid at a PCR efficiency equal to a PCR efficiency of the signal suppressor; and wherein the quantity of signal suppressor required to achieve a required threshold is the product of a number of primer molecules and a threshold amount divided by a lower limit of detection.

10. The method of claim 1, wherein the amplification step comprises polymerase chain reaction and the DNA primers amplify the target nucleic acid at a PCR efficiency different from the PCR efficiency of the signal suppressor; and wherein the quantity of signal suppressor used in the amplification step is at least the quantity S as defined in the equation:

$$S = \left(\frac{P \times Ta \times y^n}{LLOD \times x^n}\right)$$

wherein P is a number of primer molecules, Ta is a threshold amount, y is a quantity of an efficiency of amplification of the target nucleic acid, n is a number of cycles of polymerase chain reaction, LLOD is a lower limit of detection of the detection step, and x is an efficiency of the amplification of the signal suppressor raised to the nth power.

11. The method of claim 1, wherein the amplification step comprises helicase dependent amplification and the DNA primers amplify the target nucleic acid at amplification rate different from the amplification rate of the signal suppressor;
wherein the quantity of signal suppressor nucleic acid used in the amplification step is at least the quantity S as defined in the equation:

$$S = \frac{(P \times Ta \times e^{k_2 t - k_1 t})}{LLOD}$$

wherein P is the number of primer molecules, Ta is the threshold amount, k2 is the amplification rate of the target nucleic acid, k1 is the amplification rate of the signal suppressor, t is amplification time, and LLOD is the lower limit of detection.

12. The method of claim 1, further comprising determining the lower limit of detection of a detection method utilized to analyze the product of the nucleic acid amplification.

13. The method of claim 1, further comprising determining an amplification rate of the target cell nucleic acid.

14. The method of claim 1, further comprising determining an amplification rate of the signal suppressor.

15. A method of determining whether a sample contains at least 500 colony forming units per milliliter of *Staphylococcus* comprising:

providing a sample suspected of having *Staphylococcus*;
adding at least one signal suppressor nucleic acid to the sample in a quantity sufficient to ensure that amplification of a nucleic acid sequence from *Staphylococcus* will not proceed to detectable levels unless there are at least 500 colony forming units present;
subjecting the sample to a nucleic acid amplification reaction using an amplification mixture comprising a DNA polymerase, a deoxyribonucleotide triphosphate mixture, and at least one pair of DNA primers, each of the pair of DNA primers having a sequence that anneals to the signal suppressor nucleic acid and the nucleic acid sequence from *Staphylococcus*; and
detecting a signal from a product of the nucleic acid amplification reaction to determine whether at least 500 colony forming units of *Staphylococcus* are present.

16. The method of claim 15, wherein the nucleic acid amplification reaction is a helicase-dependent amplification.

17. The method of claim 15, wherein the nucleic acid amplification reaction is a polymerase chain reaction.

18. The method of claim 15, wherein the at least one pair of DNA primers are biotinylated.

19. The method of claim 15, wherein the step of detecting a signal comprises hybridization of the product of the nucleic acid amplification reaction to immobilized complementary DNA strands to yield a hybridized sample.

20. The method of claim 15, wherein the at least one pair of DNA primers amplify a specific gene sequence chosen from the group consisting of a mecA-specific gene sequence, a tuf-specific gene sequence, and a nuc-specific gene sequence.

21. A method of determining whether a sample contains a threshold amount of a target cell population, comprising:
identifying at least one type of target cell to detect from a sample;
identifying a threshold amount above which amplification of a target nucleic acid from the target cell is noncontaminating;
adding at least one signal suppressor nucleic acid for each type of target cell to the sample in a quantity sufficient to ensure that amplification of the target nucleic acid of each type of target cell will not proceed to detectable levels if the target cell is present in a quantity below the threshold amount;
amplifying the nucleic acid of the target cell in an amplification step with a DNA polymerase, a deoxyribonucleotide triphosphate mixture, and at least one pair of DNA primers, each of the pair of DNA primers having a sequence that anneals to a signal suppressor nucleic acid and the target nucleic acid,
wherein the amplification step comprises polymerase chain reaction and the DNA primers amplify the target nucleic acid with a PCR efficiency equal to a PCR efficiency of the signal suppressor nucleic acid;
wherein the quantity of signal suppressor nucleic acid is at least the quantity S as defined in the equation:

$$S = \frac{(P \times Ta \times e^{k_2 t - k_1 t})}{LLOD}$$

wherein P is the number of primer molecules, Ta is the threshold amount, k2 is the amplification rate of the target nucleic acid, k1 is the amplification rate of the signal suppressor, t is amplification time, and LLOD is the lower limit of detection; and
detecting a signal from the product of the amplification step to determine whether the target cell is present in a noncontaminating quantity.

* * * * *